US011345967B2

(12) United States Patent
Morris

(10) Patent No.: US 11,345,967 B2
(45) Date of Patent: May 31, 2022

(54) TISSUE PREPARATION USING NUCLEASE

(71) Applicant: Paradigm Diagnostics, Phoenix, AZ (US)

(72) Inventor: Scott Morris, Phoenix, AZ (US)

(73) Assignee: PARADIGM DIAGNOSTICS, Ann Arbor, MI (US)

( * ) Notice: Subject to any disclaimer, the term of this patent is extended or adjusted under 35 U.S.C. 154(b) by 72 days.

(21) Appl. No.: 16/879,585

(22) Filed: May 20, 2020

(65) Prior Publication Data

US 2020/0370128 A1 Nov. 26, 2020

Related U.S. Application Data

(60) Provisional application No. 62/851,841, filed on May 23, 2019.

(51) Int. Cl.
C12Q 1/6886 (2018.01)
C12N 15/10 (2006.01)
C12Q 1/6874 (2018.01)

(52) U.S. Cl.
CPC ....... *C12Q 1/6886* (2013.01); *C12N 15/1093* (2013.01); *C12Q 1/6874* (2013.01); *C12Q 2600/106* (2013.01); *C12Q 2600/136* (2013.01)

(58) Field of Classification Search
None
See application file for complete search history.

(56) References Cited

U.S. PATENT DOCUMENTS

| | | | |
|---|---|---|---|
| 6,177,244 B1 | 1/2001 | Sytkowski et al. | |
| 6,287,777 B1 | 9/2001 | Sytkowski et al. | |
| 6,713,062 B1 | 3/2004 | Merchant | |
| 7,029,861 B1 | 4/2006 | Beutler et al. | |
| 7,083,957 B2 | 8/2006 | Rosenblum et al. | |
| 7,285,635 B2 | 10/2007 | Rosenblum et al. | |
| 7,341,552 B2 | 3/2008 | Zhang et al. | |
| 7,482,017 B2 | 1/2009 | Barrett et al. | |
| 7,531,318 B2 | 5/2009 | Srivastava et al. | |
| 7,595,159 B2 | 9/2009 | Scherzer et al. | |
| 7,723,036 B2 | 5/2010 | Racila et al. | |
| 7,741,278 B2 | 6/2010 | Rosenblum et al. | |
| 7,799,519 B2 | 9/2010 | Caprioli | |
| 7,943,571 B2 | 5/2011 | Rosenblum et al. | |
| 8,138,311 B2 | 3/2012 | Rosenblum et al. | |
| 9,206,418 B2 | 12/2015 | Armour | |
| 9,422,592 B2 | 8/2016 | Morris et al. | |
| 9,650,628 B2 | 5/2017 | Amorese et al. | |
| 9,745,614 B2 | 8/2017 | Schroeder | |
| 9,765,385 B2 | 9/2017 | Rounseville et al. | |
| 9,856,521 B2 | 1/2018 | Stevens et al. | |
| 9,914,967 B2 | 3/2018 | Church et al. | |
| 9,957,549 B2 | 5/2018 | Armour et al. | |
| 10,036,012 B2 | 7/2018 | Amorese et al. | |
| 10,100,358 B2 | 10/2018 | Liu et al. | |
| 2002/0137135 A1 | 9/2002 | Sytkowski et al. | |
| 2003/0148421 A1 | 8/2003 | Newgard et al. | |
| 2003/0176331 A1 | 9/2003 | Rosenblum et al. | |
| 2004/0018522 A1 | 1/2004 | Dangond et al. | |
| 2004/0053277 A1 | 3/2004 | Zhang et al. | |
| 2006/0062806 A1 | 6/2006 | Kwon | |
| 2006/0115834 A1 | 6/2006 | Racila et al. | |
| 2006/0121496 A1 | 6/2006 | Srivastava et al. | |
| 2006/0134664 A1 | 6/2006 | Scherzer et al. | |
| 2006/0223122 A1 | 10/2006 | Fogo et al. | |
| 2007/0031900 A1 | 2/2007 | Caprioli | |
| 2007/0036780 A1 | 2/2007 | Rosenblum et al. | |
| 2007/0037194 A1 | 2/2007 | Sutcliffe et al. | |
| 2007/0128626 A1 | 6/2007 | Racila et al. | |
| 2007/0191262 A1 | 8/2007 | Racila et al. | |
| 2008/0268451 A1 | 10/2008 | Seligmann et al. | |
| 2008/0292544 A1 | 11/2008 | Rosenblum et al. | |
| 2010/0247518 A1 | 9/2010 | Rosenblum et al. | |
| 2011/0065130 A1 | 3/2011 | Caprioli | |
| 2011/0263448 A1 | 10/2011 | Croze et al. | |
| 2011/0288275 A1 | 11/2011 | Rosenblum et al. | |
| 2013/0123335 A1 | 5/2013 | Kipp et al. | |

(Continued)

FOREIGN PATENT DOCUMENTS

WO WO 1995/024498 A1 9/1995

OTHER PUBLICATIONS

Do et al., "Sequence Artifacts in DNA from Formalin-Fixed Tissues: Causes and Strategies for Minimization," Clin. Chem. 2015, 61(1):64-71. (Year: 2015).*
Bibikova, Marina, et al. "Genome-wide DNA methylation profiling using Infinium assay" Epigenomics, vol. 1, No. 1 (2009).
Do, Hongdo, and Alexander Dobrovic. "Sequence artifacts in DNA from formalin-fixed tissues: causes and strategies for minimization." *Clinical chemistry* 61.1 (2015): 64-71.
Chen, Guoli, et al. "Cytosine deamination is a major cause of baseline noise in next-generation sequencing." *Molecular diagnosis & therapy* 18.5 (2014): 587-593.
Do, Hongdo, et al. "Reducing sequence artifacts in amplicon-based massively parallel sequencing of formalin-fixed paraffin-embedded DNA by enzymatic depletion of uracil-containing templates." *Clinical chemistry* 59.9 (2013): 1376-1383.

(Continued)

*Primary Examiner* — Kaijiang Zhang
(74) *Attorney, Agent, or Firm* — Casimir Jones, S.C.; Mary Ann D. Brow

(57) ABSTRACT

The disclosed technology relates to a method of analyzing a tissue sample. In one aspect, the method comprises obtaining a formalin-fixed paraffin-embedded (FFPE) tissue sample; contacting the tissue sample with Mung Bean Nuclease to cleave mismatched DNA pairs when isolating DNA from the tissue sample; and performing an analysis on the non-digested DNA. In one embodiment, the tissue sample is obtained from a patient having a refractory disease or a cancer during biopsy, and the analysis comprises performing next-generation DNA sequencing to evaluate genomic DNA mutations. In another embodiment, the method further comprises using a computer to screen for one or more therapies according to the cancer diagnosis; and producing a computer-generated report of possible therapies.

20 Claims, 3 Drawing Sheets

(56) References Cited

U.S. PATENT DOCUMENTS

| | | | |
|---|---|---|---|
| 2013/0295590 A1 | 11/2013 | Degraff et al. | |
| 2014/0349294 A1 | 11/2014 | Church et al. | |
| 2015/0191770 A1 | 7/2015 | Rounseville et al. | |
| 2015/0292007 A1 | 10/2015 | Church et al. | |
| 2016/0222447 A1 | 8/2016 | Stevens et al. | |
| 2016/0265027 A1 | 9/2016 | Sanches-Kuiper et al. | |
| 2016/0265036 A1 | 9/2016 | Rounseville et al. | |
| 2017/0022551 A1* | 1/2017 | Liu et al. | C12Q 1/6848 |
| 2017/0082606 A1 | 3/2017 | Caprioli et al. | |
| 2017/0101671 A1 | 4/2017 | Stevens et al. | |
| 2017/0114124 A1 | 4/2017 | Wu et al. | |
| 2018/0045727 A1* | 2/2018 | Spetzler et al. | G16B 20/20 |
| 2018/0052169 A1 | 2/2018 | Kraus et al. | |
| 2018/0195119 A1 | 7/2018 | Liu et al. | |
| 2018/0230533 A1 | 8/2018 | Church et al. | |
| 2018/0237864 A1 | 8/2018 | Imler et al. | |

OTHER PUBLICATIONS

GeneRead DNA FFPE Handbook (2014): 1-21.
GeneRead DNA FFPE Kit, Part 1 (2016): 1-2.
GeneRead DNA FFPE Kit, Part 2 (2016): 1-2.
Gray Jr, Horace B., et al. "Extracellular nucleases of Pseudomonas BAL 31. I. Characterization of single strand-specific deoxyriboendonuclease and double-strand deoxyriboexonuclease activities." *Nucleic acids research* 2.9 (1975): 1459-1492.
Heyn, Patricia, et al. "Road blocks on paleogenomes—polymerase extension profiling reveals the frequency of blocking lesions in ancient DNA." *Nucleic acids research* 38.16 (2010): e161-e161.
Ishino, Sonoko, et al. "Identification of a mismatch-specific endonuclease in hyperthermophilic Archaea." *Nucleic acids research* 44.7 (2016): 2977-2986.
Kapabiosystems Technical Data Sheet. "KAPA Frag Kit for Enzymatic Fragmentation" KR1141-v3.16 (2016): 1-12.
Kapabiosystems Technical Data Sheet. "KAPA HyperPius Kit" KR1145-V3.16 (2016): 1-20.
Morris, Scott, et al. "Performance of next-generation sequencing on small tumor specimens and/or low tumor content samples using a commercially available platform." PLoS One 13(4): e0196556. (2018) 1-9.
O'Neil, Dominic, et al. "A new method for DNA extraction and artifact removal from FFPE samples for next-generation sequencing experiments." QIAGEN.
O'Neil, Dominic, et al. "Removal of sequence artifacts in FFPE samples during DNA extraction improves next-generation sequencing results." QIAGEN.
Paradigm Cancer Diagnostic Test Requisition Form.
Paradigm Cancer Diagnostics (PCDx) Testing Information Pamphlet.
Paradigm Cancer Diagnostic Sample Report.
Till, Bradley J., et al. "Mismatch cleavage by single-strand specific nucleases." *Nucleic Acids Research* 32.8 (2004): 2632-2641.
Yoon, Jung-Hoon, et al. "Human thymine DNA glycosylase (TDG) and methyl-CpG-binding protein 4 (MBD4) excise thymine glycol (Tg) from a Tg: G mispair." Nucleic acids research 31.18 (2003): 5399-5404.
Zhenming, Yu, et al. Mung Bean Nuclease Treatment Increases Capture Specificity of Microdroplet-PCR Based Targeted DNA Enrichment. PLoS One, 9(7), p. e103491.

* cited by examiner

TISSUE PREPARATION USING NUCLEASE

CROSS-REFERENCE TO RELATED APPLICATIONS

This application claims priority to U.S. Provisional Application No. 62/851,841, filed May 23, 2019, the content of which is incorporated by reference in its entirety.

BACKGROUND OF THE INVENTION

Field of the Invention

The disclosed technology relates to a method of analyzing a tissue sample, and more particularly, to a method of performing a cancer diagnosis by removing unwanted nucleic acids with a mismatch nuclease.

Description of the Related Art

Cancer is a major health risk in the United States and internationally. A robust test that provides patients and physicians with a blueprint of the underlying mechanisms of a patient's disease, genomic and proteomic information about a patient's cancer, potential treatment approaches, and comprehensive inventory of relevant clinical trials would be of substantial benefit for the treatment of cancer and would help the oncologist personalize each patient's course of treatment.

Because formalin-fixed paraffin-embedded (FFPE) tissue can be stored and transported at ambient conditions, it is a commonly used tissue preparation for cancer diagnosis and analysis. However, formaldehyde being a major component of formalin is reactive with DNA bases, proteins, and oxygen. FFPE tissue samples often contain formaldehyde-induced crosslinks, DNA fragmentations, and DNA lesions such as abasic sites, mismatch, and modified bases. These artifacts cause problems in interpreting DNA sequencing results, which lead to false-positives in the detection of DNA mutations in cancer diagnosis.

For example, deamination of cytosine bases to uracil or deamination of 5-methylcytosine to thymine are present in FFPE DNA, causing mismatch in the DNA and apparent C:G>T:A sequencing result as DNA polymerase incorporates an adenine opposite to uracil lesions or thymine lesions. Treatment of FFPE DNA with uracil-DNA glycosylase (UDG) before PCR-based sequencing can reduce apparent C:G>T:A single-nucleotide changes due to uracil lesions. However, UDG treatment fails to cure apparent C:G>T:A single-nucleotide changes due to thymine lesions. It was suggested that thymine lesions may be removed using the repair enzymes thymine DNA glycosylase (TDG) and methyl-CpG-binding protein 4 (MBD4). In addition, low bypass efficiency DNA polymerases such as Pfu and KAPA can be used to block amplification of damaged DNA.

A wider array of strategies for removing artifacts in FFPE samples, as well as improvements in the efficiency, are still being developed.

SUMMARY OF THE INVENTION

One objective of some aspects of the disclosed technology is to reduce artifacts that occur in FFPE tissues and improve the analysis of DNA.

One embodiment is a method of analyzing a tissue sample. The method may include: obtaining a tissue sample; isolating DNA from the tissue sample; contacting the tissue sample with a nuclease that digests mismatched DNA pairs in the DNA; removing the digested DNA; and performing an analysis on the non-digested DNA. One aspect of the disclosed technology is use of a nuclease that digests mismatched DNA pairs in a method of analyzing a tissue sample for the presence of cancer. The method of analyzing the tissue sample may include contacting the tissue sample with uracil-N-glycosylase, uracil-DNA glycosylase, thymine DNA glycosylase, methyl-CpG-binding protein 4, or any combination thereof, to remove mismatched DNA bases. The method may further include performing a next-generation DNA sequencing analysis on: single nucleotide variants and insertions/deletions up to 40 basepairs in coding regions of a plurality of target genes; gene copy number variations; untranslated regions and splice junctions of the DNA; gene fusions; microsatellite instability; and/or tumor mutation burden. The nuclease may be Mung Bean Nuclease, CEL I, Surveyor nuclease, *aspergillus* nuclease S1, P1 nuclease, BAL 31, T4 endonuclease VII, T7 endonuclease I, endonuclease V, EndoMS, RecJ$_f$, or any combination thereof. The tissue sample may be a formalin-fixed paraffin-embedded (FFPE) tissue sample, fresh-frozen sample, freshly cut curls, or freshly cut slides.

DETAILED DESCRIPTION

All patents, applications, published applications and other publications referred to herein are incorporated herein by reference to the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

Embodiments relate to methods for analyzing tissue samples to determine if the sample contains cancer or tumorigenic cells. Next Generation Sequencing (NGS) is increasingly utilized for patients with advanced cancer in an effort to help guide treatment, especially for tumor types that have potential targeted therapy options. In many cases, samples to be tested are stored as FFPE samples prior to NGS analysis. While the FFPE process helps preserve the tissue, environmental and other issues may affect the quality of the final sample and reduce the efficacy of the NGS analysis. For example, high heat conditions during storage or transport may degrade the nucleic acids in the sample. Similarly, freeze/thaw cycles of FFPE samples may subject the tissue to stress, which reduces the quality of the nucleic acids in the sample.

One additional aspect of the disclosed technology is use of a nuclease that digests mismatched DNA pairs in a method of analyzing a tissue sample for the presence of cancer. In this use, analyzing the tissue sample may include: obtaining a tissue sample; isolating DNA from the tissue sample; contacting the tissue sample with a nuclease that digests mismatched DNA pairs in the DNA; removing the digested DNA; and performing an analysis on the non-digested DNA. The use may include contacting the tissue sample with uracil-N-glycosylase, uracil-DNA glycosylase, thymine DNA glycosylase, methyl-CpG-binding protein 4, or any combination thereof, to remove mismatched DNA bases. The use may further include performing a next-generation DNA sequencing analysis on: single nucleotide variants and insertions/deletions up to 40 basepairs in coding regions of a plurality of target genes; gene copy number variations; untranslated regions and splice junctions of the DNA; gene fusions; microsatellite instability; and/or tumor mutation burden. The nuclease may be Mung Bean Nuclease, CEL I, Surveyor nuclease, *aspergillus* nuclease S1, P1 nuclease, BAL 31, T4 endonuclease VII, T7 endonuclease I, endonuclease V, EndoMS, RecJf, or any combination thereof. The tissue sample may be a formalin-fixed paraffin-embedded (FFPE) tissue sample, fresh-frozen sample, freshly cut curls, or freshly cut slides.

Figure 1:
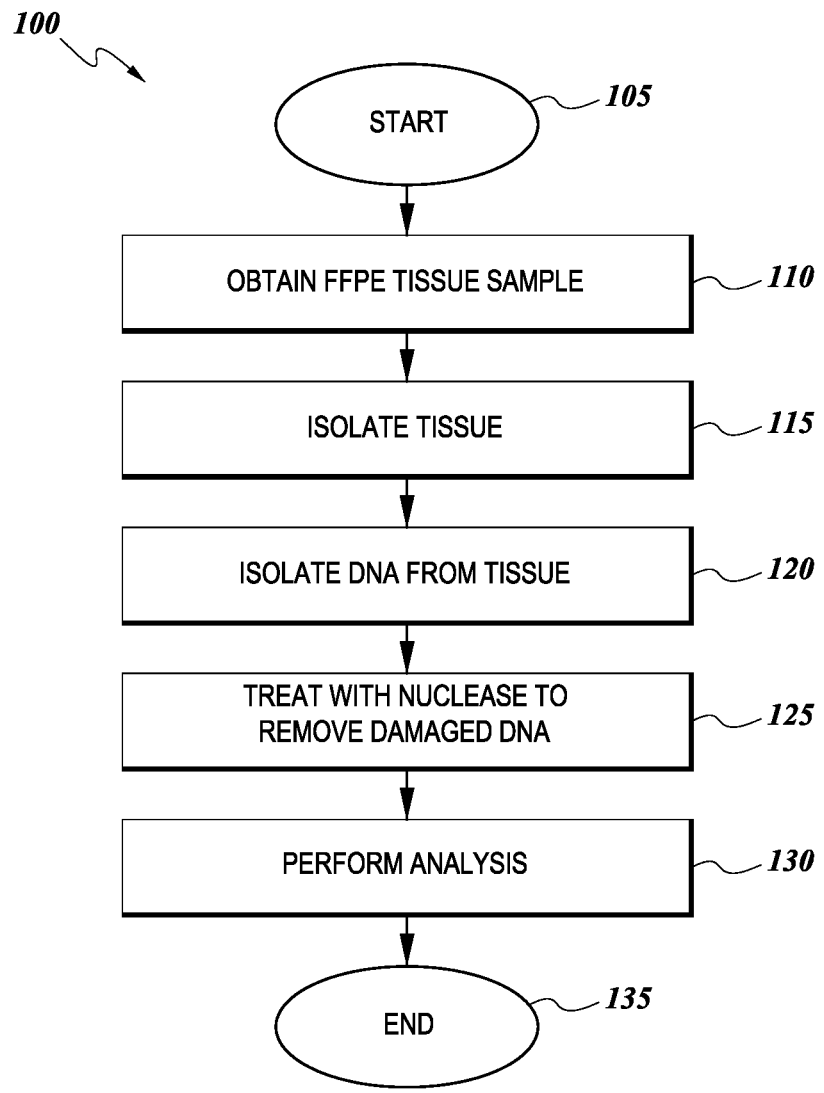
FIG. 1 illustrates an exemplary workflow of one method of analyzing a tissue sample.

One embodiment is shows in the flow diagram of FIG. 1. As shown, the process 100 begins at a start state 105 and then moves to a state 110, wherein an FFPE tissue sample is obtained. As discussed below, the tissue may be obtained from a patient suspected of having cancer, or where the patient is known to have cancer, but a more thorough analysis of the type of cancer may be desired. The process 100 then moves to state 115 where the tissue to be analyzed is isolated from the FFPE sample, as discussed in more detail below. Once the tissue has been isolated, the process 100 moves to state 120 where DNA is extracted from the tissue by well-known methods. After the DNA is extracted, it is treated with a nuclease to remove damaged DNA from the analysis according to embodiments of the invention. In one embodiment the nuclease is the Mung Bean Nuclease which digests mismatched DNA from a DNA double strand. This step increases the quality of the resulting DNA since artifacts that may have arisen during the tissue-processing step can be removed since normal double stranded DNA should not have single base pair mismatches in the double stranded DNA samples. Once the nuclease has been used to remove damaged DNA from the sample at state 125, the process 100 moves to a state 130 wherein an analysis, such as by Next Generation Sequencing, can be performed on the sample. The process 100 then terminates at an end state 135.

In one embodiment, the quality of a tissue sample for NGS analysis is improved by contacting the sample with a mismatch enzyme that digests mismatched strands in the double stranded DNA of a tissue sample during analysis. Many of the factors affecting the quality of a sample may lead to a single basepair mutation in the tissue DNA. This single base pair mutation will present itself as a mismatch in any DNA that has been modified. Thus, in one embodiment, the mismatched DNA is digested using a specific enzyme and removed from the analysis. By removing the mismatched DNA, the background noise caused by artificially mutated DNA is reduced. The DNA remaining after such digestion would more properly reflect the original sample DNA since artificially mutated DNA is removed. Examples of mismatch enzymes include Mung Bean Nuclease, which degrades single-stranded DNA or RNA to nucleoside 5'-monophosphates, but does not digest double-stranded DNA, double-stranded RNA, or DNA/RNA hybrids. Mung Bean Nuclease catalyzes the specific degradation of single-stranded DNA or RNA, and produces mono and oligonucleotides carrying a 5'-P terminus, Other examples mismatch enzymes or single-stranded DNA specific endo- or exo-nucleases include CEL I, Surveyor nuclease, *aspergillus* nuclease S1, P1 nuclease, BAL 31, T4 endonuclease VII, T7 endonuclease I, endonuclease V, EndoMS, and RecJf.

In one embodiment, the specimen being analyzed is taken from a patient who has undergone surgery or a biopsy. For example, the tissue may come from freshly cut shaves/curls along with hematoxylin and eosin stained section of the same block. The tissue may come from freshly cut, unstained, unbaked sections on positively charged slides. In one embodiment, the specimen is approximately 75 mm$^3$ (5 mm×5 mm×3 mm) in size, and may have been taken from 4 to 6 needle biopsies. In one embodiment, the specimen has 20%, 30%, 40%, 50%, 60% or higher tumor content. In one embodiment, the minimally required amount of a tissue specimen is from one core needle biopsy with approximately 10%, 15% or 20% tumor content.

After the specimen is obtained, it may be fixed in buffered formalin containing 4% formaldehyde in 1× phosphate-buffered saline to preserve the tissue and its cellular morphology. The specimen may be fixed by immersing the specimen in about a 20× or larger volume of buffered formalin for 14-24 hours, at 4° C. or room temperature. After fixing, the specimen may be washed several times in 1× phosphate-buffered saline to remove the formalin from the specimen.

After formalin fixation, the specimen may be embedded into paraffin. During this process, the specimen is dehydrated by graded ethanol baths to gradually displace the water within the tissue. The specimen may then be infiltrated with melted paraffin wax. The paraffin wax may have a melting point of about 56° C.-58° C., or up to 65° C.-70° C. in some embodiments. By immersing the specimen in molten paraffin wax kept at about 2° C. above the melting point the tissue sample will become embedded within the wax. After immersing the specimen into the melted paraffin, the infiltrated specimen may be formed into a paraffin wax block by placing the infiltrated specimen into a mold to form the block. In some embodiments, a margin of 1, 2, 3, 4, 5 or more millimeters or more of wax may be left surrounding the specimen.

Alternatively, the specimen may be embedded into paraffin in a different manner preferred by local procedures within various pathology departments or hospitals. Once the tissue is embedded into a paraffin block, the formalin-fixed paraffin-embedded (FFPE) specimen may then be shipped to a lab for analysis by the methods described herein. Specimens may be shipped by mail using an overnight service, for example, in a styrofoam container with an ice pack.

One embodiment is a method of analyzing a tissue sample taken from a patient, wherein the tissue sample is contacted with with a nuclease that digests mismatched DNA pairs in the DNA prior to performing an analysis on the non-digested DNA. In one embodiment, the tissue sample is further contacted with uracil-N-glycosylase, uracil-DNA glycosylase, thymine DNA glycosylase, methyl-CpG-binding protein 4, or any combination thereof, to remove mismatched DNA bases before, during, or after contact with a prior mismatched DNA enzyme. The tissue sample under analysis may be from a formalin-fixed paraffin-embedded (FFPE) tissue sample, fresh-frozen sample, or freshly cut curls from a patient.

In one embodiment, the tissue sample is obtained from the bone, bone marrow, breast, mouth, nasopharynx, esophagus, stomach, duodenum, rectum, colon, intestine, appendix, pancreas, lung, liver, prostate, nervous system, heart, bladder, kidney, cervix, uterus, ovary, lymph node, thyroid, muscle, or skin of a subject, the subject being a mammal, such as a human patient having a refractory disease or a cancer. In one embodiment, the tissue sample is derived from a stereotactic biopsy, open biopsy, or surgical resection.

In one embodiment, the analysis performed on the tissue sample following treatment is a NGS analysis, including analysis of single nucleotide variants, insertions/deletions, gene copy number variations; untranslated regions and splice junctions of the DNA; gene fusions; microsatellite instability; and/or tumor mutation burden. In one embodiment, the NGS analysis includes tagging each strand of DNA isolated form the sample with a duplex unique molecular identifier (UMI). In one embodiment, the NGS analysis includes amplifying the isolated DNA with a low bypass efficiency DNA polymerase, for example Pfu or KAPA.

During the NGS analysis, a plurality of different genes may be analyzed to determine the characteristics of the tumor sample under analysis. This may involve analysis of one or more target genes to look for polymorphisms, such as single nucleotide polymorphisms (SNPs) within the target gene. The target genes may include one or more of: ABCB1, ABCC1, ABCC2, ABL1, ADAMTS1, ADAMTS16, ADAMTS18, ADAMTS6, ADAMTS9, ADAMTSL1, AKT1, AKT2, AKT3, ALK, AMER1, APC, APLNR, AR, ARAF, AREG, ARID1A, ARID1B, ARID2, ATM, ATR, ATRX, AURKA, AURKB, AXIN1, AXL, B2M, BAP1, BARD1, BCOR, BNIP3, BRAF, BRCA1, BRCA2, BRIP1, BTK, BUB1B, CBL, CCND1, CCND2, CCND3, CCNE1, CD274, CDA, CDC73, CDH1, CDK12, CDK4, CDK6, CDKN2A, CHEK1, CHEK2, CHFR, CHKA, CIC, CREBBP, CSF1R, CTLA4, CTNNB1, CYP19A1, CYP1A1, CYP2D6, CYP3A4, CYSLTR2,DCK, DDR2, DICER1, DNMT3A, EGFR, EMSY, EP300, EPCAM, EPHA5, EPHA7, ERBB2, ERBB3, ERBB4, ERCC1, ERCC2, ERCC3, ERRFI1, ESR1, ESR2, EWSR1, EZH2, FAM175A, FANCA, FANCC, FANCD2, FANCE, FANCF, FANCG, FANCM, FAT1, FBXW7, FCGR2A, FGD4, FGF3, FGF4, FGFR1, FGFR2, FGFR3, FGFR4, FLT3, FLT4, FOXL2, FUBP1, GATA3, GLI1, GNA11, GNAQ, GNAS, GSTP1, GSTT1, HDAC2, HGF, HNF1A, HRAS, HSD3B1, IDH1, IDH2, IGF1R, IKZF1, JAK1, JAK2, JAK3, KDM5C, KDM6A, KDR, KEAP1, KIT, KRAS, MAF, MAP2K1, MAP2K2, MAP3K1, MAPK1, MAPK3, MAPKAPK5, MDM2, MDM4, MED12, MEN1, MET, MGMT, MLH1, MRE11A, MSH2, MSH6, MTHFR, MTOR, MUTYH, MYC, MYCN, MYOD1, NBN, NF1, NF2, NFE2L2, NOTCH1, NOTCH2, NOTCH3, NPM1, NRAS, NTRK1, NTRK2, NTRK3, PALB2, PBRM1, PDCD1LG2, PDGFRA, PDGFRB, PIK3CA, PIK3CB, PIK3CD, PIK3CG, PIK3R1, PLCB4, PLCG1, PMS2, POLD1, POLE, PPP2R1A, PTCH1, PTEN, PTPN11, RAD50, RAD51C, RAD51D, RAF1, RB1, RBM10, RECQL, RET, RHEB, RICTOR, RIT1, RNF43, ROS1, RPTOR, RRM1, SDHB, SDHC, SETD2, SF3B1, SMAD2, SMAD4, SMARCA4, SMARCB1, SMO, SOCS1, SPOP, STAG2, STATS, STK11, SUFU, TERT-p, TGFBR2, TNFAIP3, TOP2A, TP53, TSC1, TSC2, TSHR, TYMS, VEGFA, VHL, WT1, XRCC1, and YES1.

In one embodiment, the analysis of the DNA may further include performing an analysis on mRNA expression and/or gene isoforms of a plurality of target genes. In one embodiment, the analysis includes in situ hybridization, reverse transcription-polymerase chain reaction, microarray, nuclease protection assays, or RNA sequencing.

In one embodiment the plurality of target genes comprise: AR, AREG, ARID1A, BAD, BAX, BCL2, BIRC5, BRCA1, CA9, CDA, CDH1, CES2, CHUK, DCK, DHFR, DPYD, EPHA2, ERBB2, ERBB3, ERCC1, EREG, ESR1, EZH2, FGFR1, IGF1R, KDR, KIT, LRP6, MET, MGMT, MITF, MTOR, NFKB1, PARP1, PDGFRB, PGR, PTEN, PTGS2, PTPN6, RELA, RPS6KB1, RRM1, SLC29A1, SSTR2, TNFSF13, TOP2A, TUBB3, TYMP, TYMS, VEGFA, EGFR VIII, and MET EXON 14 SKIPPING.

In one embodiment, the analysis includes performing an immunohistochemistry analysis on one or more proteins that are expressed by the cells in the tissue under analysis. The target proteins may include ALK, AR, CAIX, ER, hENT1, HER2/neu, PD1, PD-L1, PMS2, PR, PTEN, RET, IDO, MET, MGMT, MLH1, MSH2, MSH6, ROS1, TOPO1, TP, TRKpan, TS, and TUBB3.

The analysis may also include performing a cancer diagnosis and, optionally, detecting DNA mismatch repair deficiency. In this embodiment, the cancer may include one or more of breast cancer, colorectal cancer, lynch syndrome, non-small-cell lung carcinoma, acute lymphoblastic leukemia, acute myeloid leukemia, adrenocortical carcinoma, aids-related cancers, Kaposi sarcoma, aids-related lymphoma, primary CNS lymphoma, anal cancer, appendix cancer, astrocytomas, atypical teratoid/rhabdoid tumor, basal cell carcinoma of the skin, bile duct cancer, bladder cancer, bone cancer, brain tumors, bronchial tumors, Burkitt lymphoma, carcinoid tumor, carcinoma of unknown primary, cardiac tumors, cervical cancer, cholangiocarcinoma, chronic lymphocytic leukemia, chronic myelogenous leukemia, chronic myeloproliferative neoplasms, craniopharyngioma, cutaneous T-cell lymphoma, ductal carcinoma in situ, embryonal tumors, endometrial cancer, esophageal cancer, esthesioneuroblastoma, Ewing sarcoma, extragonadal germ cell tumor, eye cancer, intraocular melanoma, retinoblastoma, fallopian tube cancer, fibrous histiocytoma of bone, gallbladder cancer, gastric cancer, gastrointestinal carcinoid tumor, gastrointestinal stromal tumors, germ cell tumors, extragonadal germ cell tumors, ovarian germ cell tumors, testicular cancer, gestational trophoblastic disease, hairy cell leukemia, head and neck cancer, hepatocellular cancer, histiocytosis, Hodgkin lymphoma, hypopharyngeal cancer, intraocular melanoma, islet cell tumors, pancreatic neuroendocrine tumors, kidney cancer, Langerhans cell histiocytosis, laryngeal cancer, leukemia, lip and oral cavity cancer, liver cancer, non-small cell lung cancer, lymphoma, male breast cancer, malignant fibrous histiocytoma of bone and osteosarcoma, melanoma, intraocular melanoma, Merkel cell carcinoma, mesothelioma, metastatic cancer, metastatic squamous neck cancer with occult primary, midline tract carcinoma with nut gene changes, mouth cancer, multiple endocrine neoplasia syndromes, multiple myeloma/plasma cell neoplasms, mycosis fungoides, myelodysplastic syndromes, myelodysplastic/myeloproliferative neoplasms, myelogenous leukemia, myeloid leukemia, nasal cavity and paranasal sinus cancer, nasopharyngeal cancer, neuroblastoma, non-Hodgkin lymphoma, oral cancer, osteosarcoma and malignant fibrous histiocytoma of bone, ovarian cancer, pancreatic cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, plasma cell neoplasm/multiple myeloma, pleuropulmonary blastoma, primary central nervous system lymphoma, primary peritoneal cancer, prostate cancer, rectal cancer, recurrent cancer, renal cell cancer, retinoblastoma, rhabdomyosarcoma, salivary gland cancer, sarcoma, osteosarcoma, soft tissue sarcoma, uterine sarcoma, Sézary syndrome, skin cancer, small cell lung cancer, small intestine cancer, squamous cell carcinoma of the skin, stomach cancer, testicular cancer, throat cancer, nasopharyngeal cancer, oropharyngeal cancer, hypopharyngeal cancer, thymoma and thymic carcinoma, thyroid cancer, transitional cell cancer of the renal pelvis and ureter, urethral cancer, endometrial uterine cancer, uterine sarcoma, vaginal cancer, vascular tumors, vulvar cancer, and/or Wilms tumor. The method may also include screening for one or more therapies according to the cancer diagnosis and thereafter producing an electronically generated report of therapies with potential increased benefit and therapies with potential reduced benefit.

Example of therapies that may be included as a benefit may include one or more therapies selected from: Abemaciclib, Abiraterone, Ado-trastuzumab emtansine, Afatinib, Alectinib, Anastrozole, Atezolizumab, Avelumab, Bevacizumab, Bicalutamide, Binimetinib, Brigatinib, Cabozantinib, Capecitabine, Carboplatin, Carmustine, Ceritinib, Cetuximab, Cisplatin, Crizotinib, Dabrafenib, Dacarbazine, Dacomitinib, Dasatinib, Diethylstilbestrol, Dinutuximab, Docetaxel, Doxorubicin, Durvalumab, Encorafenib, Enzalutamide, Epirubicin, Eribulin, Erlotinib, Everolimus, Exemestane, Fluorouracil, Flutamide, Fulvestrant, Gefitinib, Gemcitabine, Idelalisib, Imatinib, Interleukin-2, Ipilimumab, Irinotecan, Ketoconazole, Lapatinib, Lenvatinib, Letrozole, Liposomal Doxorubicin, Lorlatinib, Medroxyprogesterone, Megestrol, Mitomycin, Neratinib, Nilotinib, Nintedanib, Niraparib, Nivolumab, Olaparib, Olaratumab, Osimertinib, Oxaliplatin, Paclitaxel, Palbociclib, Panitumumab, Pazopanib, Pembrolizumab, Pemetrexed, Pertuzumab, Procarbazine, Regorafenib, Ribociclib, Rucaparib, Sonidegib, Sorafenib, Streptozocin, Sunitinib, Talazoparib, Tamoxifen, Temozolomide, Temsirolimus, Topotecan, Toremifene, Trametinib, Trastuzumab, Vandetanib, Vemurafenib, Vincristine, Vismodegib, Zoledronic acid, or any combination thereof.

Method of DNA Extraction

In one embodiment, once the specimen has been embedded into the FFPE it can be handled, shipped, or stored until the analysis process has been initiated. To start analyzing the quality of the specimen, and to check for DNA degradation, the FFPE specimen may be sectioned using a microtome. For example, the specimen can be cut into 4 µm, 5 µm, 6 µm, 7 µm, 8 µm, 9 µm or up to 10 µm or greater sections to be placed into slides. Optionally, macrodissection or coring of the tumor-enriched areas may lead to better sample quality. Once the slides have been prepared, the slides may be dewaxed by warming at 56° C.-60° C. in a paraffin-solubilizing organic solvent for 1 minute, 2 minutes, 3 minutes, 4 minutes, or up to 5 minutes or more. After the slides have been dewaxed, the tissue may be lysed at 56° C.-60° C. by surfactants such as sodium dodecyl sulfate, and by proteinase. Once the tissue sample has been lysed, the sample may then be heat-treated at 65° C., 70° C., 75° C., 80° C., 85° C., 90° C., or 95° C. for 1 hour to remove formaldehyde-induced DNA-DNA and DNA-protein crosslinks. In one embodiment, heat-treating at 75° C. may be set out to minimize melting of DNA. In another embodiment, heat-treating at 90° C. may be set out to maximize de-crosslinking.

After the sample has been heat-treated, the enzyme uracil-N-glycosylase (UNG) may be added to the sample. In some embodiments, the sample may then be incubated at 40° C., 45° C., 50° C., 55° C., or 60° C. for 1 hour, 2 hours, or 3 hours with UNG to remove artifacts of deaminated cytosine residues of the FFPE DNA.

Alternatively, in some embodiments, the sample may be incubated with UNG at 40° C., 45° C., 50° C., 55° C., or 60° C. for 10 minutes, 20 minutes, 30 minutes, 40 minutes, or 50 minutes. After the sample has been incubated with UNG, the sample may be cooled to room temperature, and 0.1 µL, 0.5 µL, 1 µL, 2 µL, or more Mung Bean Nuclease may be added to digest any mismatched DNA within the sample. This digestion may remove DNA from the sample that has been damaged due to environmental factors that degraded the sample prior to the sample analysis. In one embodiment, the sample is incubated for 10 minutes, 20 minutes, 30 minutes, 40 minutes, or 50 minutes at 25° C., 30° C., or 35° C. with Mung Bean Nuclease to cleave single-stranded DNA regions and base pair mismatches. As discussed above, embodiments are not limited to digestion with only Mung Bean Nuclease, other enzymes which digest mismatched DNA strands are also contemplated within the scope of the invention.

Once single-stranded DNA regions and basepair mismatches have been cleaved, the sample may then be treated with RNase at room temperature for 1 minute, 2 minutes, 3 minutes, 4 minutes, 5 minutes, or longer to remove RNA from the sample. In some embodiments, additional proteinase K treatment may be used to further remove proteins cross-linked to DNA. After RNA has been removed from the sample, to harvest the DNA, a spin column, e.g. QIAamp MinElute column, may be used to bind the DNA and contaminants may be removed by buffer-wash and centrifugal steps as specified in a commercial Kit, e.g. Qiagen GeneRead DNA FFPE Kit.

Once the DNA has been purified, assays based on DNA-specific fluorescent dyes, such as PicoGreen or Qubit fluorometer, may be used to quantify the amount of purified DNA in some embodiments.

Method of NGS Sequencing Library Construction

In some embodiments, once the genomic DNA from the tissue sample has been purified, the extracted genomic DNA may be fragmented and prepared to produce dsDNA fragments suitable for next-generation sequencing (NGS). For example, in one embodiment, enzymatic fragmentation by the KAPA Frag Enzyme may be used, as detailed in the KAPA Frag Kit or KAPA HyperPlus Kit (Kapa Biosystems). Following the KAPA HyperPlus Kit library construction protocol, the enzymatic fragmentation reaction may be incubated for 5-40 minutes at 37° C. In other embodiments, a mixture of endonucleases and dsDNA nicking enzymes may be used, and the enzymatic fragmentation reaction may be incubated for less than 30 minutes, less than 60 minutes, less than 1.5 hours, less than 2 hours, or more than 2 hours at 30-50° C.

Alternatively, in some embodiments, the enzymatic fragmentation reaction may be incubated at 30° C., with 0.1 µL, 0.5 µL, 1 µL, 2 µL, or more Mung Bean Nuclease further added to cleave single-stranded DNA regions and basepair mismatches. In yet other embodiments, the enzymatic fragmentation reaction may be incubated at 30° C., with 0.1 µL, 0.5 µL, 1 µL, 2 µL, or more RecJ$_f$ further added to cleave single-stranded DNA regions and basepair mismatches.

Subsequent to the DNA fragmentation, to prepare a DNA library suitable for next-generation sequencing, several reactions may be further performed according to the KAPA HyperPlus Kit library construction protocol, including end repair reaction to produce blunt-ended, 5'-phosphorylated DNA fragments; A-tailing of the fragments by adding dAMP to the 3'-ends of the dsDNA fragments; and adapter ligation reaction to ligate dsDNA adapters with 3'-dTMP overhangs to the 3'-dA-tailed library fragments. In other embodiments, protocols based on similar reactions may be used.

During the adapter ligation reaction, in some embodiments identification of sequence artifacts may be achieved by ligating specialized adapters to both fragment ends.

After the DNA library has been prepared, the reaction may be cleaned-up to remove digested DNA or other contaminants. After the reactions has been cleaned up, the DNA library fragments carrying appropriate adapter sequences on both ends may be amplified by PCR. In some embodiments, DNA polymerases that have low bypass efficiency over DNA lesions, such as abasic sites, may be used to alleviate some of the FFPE artifacts. In one embodiment, the Pfu DNA polymerase may be used. In another embodiment, the KAPA DNA polymerase may be used.

After the library has been amplified, in one embodiment the sample may be gel purified to select for DNA fragments with appropriate size. In another embodiment, the sample may be bead purified.

Alternatively, in some embodiments, the extracted genomic DNA may be fragmented and prepared to produce library fragments suitable for any well-known NGS platform. In one embodiment, the sequencing platform may be made by Illumina or Thermo Fisher Scientific. In some embodiments, genomic DNA fragmentation may be achieved by mechanical shearing methods. In one embodiment, DNA fragmentation may be achieved by using the Covaris Adaptive Focused Acoustics technology.

Alternative to fragmenting the genomic DNA sample and then ligating specialized adapters, in some embodiments, the library preparation may be achieved by a tagmentation reaction, using a transposon to cleave and tag the double-stranded DNA with a universal overhang, followed by limited cycle PCR to add sequencing primer sequences and indexes.

Once the DNA from the sample has been sequenced, a determination can be made whether the sample contains cancer or other markers of a disease. In addition, the sample may be analyzed to determine what potential treatments are available for the patient who submitted the sample based on the genomic information discovered from the sequence information.

Definitions

As used herein, the singular forms "a", "an", and "the" include plural references unless indicated otherwise, expressly or by context. For example, "a" dimer includes one or more dimers, unless indicated otherwise, expressly or by context.

EXAMPLES

The following examples are offered to illustrate but not to limit the invention. In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1

Sample Handling

Three FFPE blocks of normal tissues of low quality (EXO-0000771), moderate quality (EXO-0000338), and high quality (EXO-0000808), respectively, were selected. Excess paraffin was trimmed off from each block. Each FFPE block was sectioned using a microtome to obtain five 4 μm slides. Each slide was placed into a separate microcentrifuge tube.

Example 2

DNA Extraction and Library Preparation—Group A

Three FFPE slides of low quality, moderate quality, and high quality, respectively, were processed according to the DNA purification protocol of Qiagen GeneRead DNA FFPE Kit, followed by the library construction protocol of KAPA HyperPlus Kit.

Briefly, the slides were dewaxed by warming at 56° C. in 160 μL Deparaffinization Solution for 3 minutes. The tissues were lysed at 56° C. for 1 hour in 55 μL RNase-free water, 25 μL Buffer FTB, and 20 μL proteinase K. The tissues were then heat-treated at 90° C. for 1 hour to de-crosslink. After the heat treatment, the tissues were centrifuged and transferred to new microcentrifuge tubes. Then, 115 μL RNase-free water and 35 μL of the enzyme uracil-N-glycosylase (UNG) were added to the samples, and the samples were incubated at 50° C. for 1 hour to remove artifacts of deaminated cytosine residues of the FFPE DNA. The samples were then treated with 2 μL RNase A at room temperature for 2 minutes. To harvest the DNA, the QIAamp MinElute columns were used to bind the DNA while contaminants were removed by buffer-wash and centrifugal steps as specified in the DNA purification protocol. Finally, DNA was eluted in 20 μL Buffer ATE. The amount of extracted DNA was quantified by the Qubit fluorometer.

The extracted genomic DNA was diluted in 10 mM Tris-HCl (pH 8.0-8.5) to 35 μL. To fragment the genomic DNA, 10 μL KAPA Frag Enzyme and 5 μL 10× KAPA Frag Buffer were added, and the enzymatic reaction was incubated for 30 minutes at 37° C., then held at 4° C. Subsequent to the DNA fragmentation, end repair and A-tailing of the fragments were performed by adding 7 μL End Repair & A-Tailing Buffer and 3 μL End Repair & A-Tailing Enzyme Mix, and rapidly heating up to 65° C. and incubating at 65° C. for 30 minutes. Then, adapter ligation was performed by adding 5 μL Adapter stock, 5 μL PCR-grade water, 30 μL Ligation Buffer, and 10 μL DNA Ligase, and incubating at 20° C. for 15 minutes.

To clean up the reaction, 88 μL KAPA Pure Beads was added. The sample was mixed thoroughly and incubated at room temperature for 10 minutes to bind DNA to the beads. The DNA and beads were captured by a magnet during several ethanol washes according to the library construction protocol, and then resuspended in 25 μL elution buffer (10 mM Tris-HCl, pH 8.0-8.5). To elute DNA off the beads, the sample was incubated at room temperature for 2 minutes. The beads were captured by the magnet while 20 μL of the supernatant containing the DNA was transferred to a new microcentrifuge tube. After cleaning up the reaction, the DNA library fragments carrying appropriate adapter sequences were amplified by PCR. 5 μL Library Amplification Primer Mix and 25 μL KAPA HiFi HotStart ReadyMix, containing the low-bias, high-fidelity KAPA HiFi HotStart DNA Polymerase, were added. A PCR cycle specified in the library construction protocol and a post-amplification cleanup, again using magnetic KAPA Pure Beads, were performed.

Example 3

DNA Extraction and Library Preparation—Group B

Three FFPE slides of low quality, moderate quality, and high quality, respectively, were processed according to the DNA purification protocol of Qiagen GeneRead DNA FFPE Kit, followed by the library construction protocol of KAPA HyperPlus Kit, but with some modifications.

Briefly, the slides were dewaxed by warming at 56° C. in 160 µL Deparaffinization Solution for 3 minutes. The tissues were lysed at 56° C. for 1 hour in 55 µL RNase-free water, 25 µL Buffer FTB, and 20 µL proteinase K. The tissues were then heat-treated at 90° C. for 1 hour to de-crosslink. After the heat treatment, the tissues were centrifuged and transferred to new microcentrifuge tubes. Then, 115 µL RNase-free water and 35 µL of the enzyme uracil-N-glycosylase (UNG) were added to the samples to remove artifacts of deaminated cytosine residues of the FFPE DNA. In contrast to Group A, here the sampled were incubated with UNG at 50° C. for 30 minutes. After incubation, the samples were cooled down to room temperature, 2 µL Mung Bean Nuclease (10 units/µL, New England BioLabs) was added to each sample, and the samples were incubated for 30 minutes at 30° C. to cleave single-stranded DNA regions and basepair mismatches. The samples were then treated with 2 µL RNase A at room temperature for 2 minutes. To harvest the DNA, the QIAamp MinElute columns were used to bind the DNA while contaminants were removed by buffer-wash and centrifugal steps as specified in the DNA purification protocol. Finally, DNA was eluted in 20 µL Buffer ATE. The amount of extracted DNA was quantified by the Qubit fluorometer.

The extracted genomic DNA was diluted in 10 mM Tris-HCl (pH 8.0-8.5) to 35 µL. To fragment the genomic DNA, 10 µL KAPA Frag Enzyme and 5 µL 10× KAPA Frag Buffer were added, and the enzymatic reaction was incubated for 30 minutes at 37° C., then held at 4° C. Subsequent to the DNA fragmentation, end repair and A-tailing of the fragments were performed by adding 7 µL End Repair & A-Tailing Buffer and 3 µL End Repair & A-Tailing Enzyme Mix, and rapidly heating up to 65° C. and incubating at 65° C. for 30 minutes. Then, adapter ligation was performed by adding 5 µL Adapter stock, 5 µL PCR-grade water, 30 µL Ligation Buffer, and 10 µL DNA Ligase, and incubating at 20° C. for 15 minutes.

To clean up the reaction, 88 µL KAPA Pure Beads was added. The sample was mixed thoroughly and incubated at room temperature for 10 minutes to bind DNA to the beads. The DNA and beads were captured by a magnet during several ethanol washes according to the library construction protocol, and then resuspended in 25 µL elution buffer (10 mM Tris-HCl, pH 8.0-8.5). To elute DNA off the beads, the sample was incubated at room temperature for 2 minutes. The beads were captured by the magnet while 20 µL of the supernatant containing the DNA was transferred to a new microcentrifuge tube. After cleaning up the reaction, the DNA library fragments carrying appropriate adapter sequences were amplified by PCR. 5 µL Library Amplification Primer Mix and 25 µL KAPA HiFi HotStart ReadyMix, containing the low-bias, high-fidelity KAPA HiFi HotStart DNA Polymerase, were added. A PCR cycle specified in the library construction protocol and a post-amplification cleanup, again using magnetic KAPA Pure Beads, were performed.

Example 4

DNA Extraction and Library Preparation—Group E

Three FFPE slides of low quality, moderate quality, and high quality, respectively, were processed according to the DNA purification protocol of Qiagen GeneRead DNA FFPE Kit, followed by the library construction protocol of KAPA HyperPlus Kit, but with some modifications.

Briefly, the slides were dewaxed by warming at 56° C. in 160 µL Deparaffinization Solution for 3 minutes. The tissues were lysed at 56° C. for 1 hour in 55 µL RNase-free water, 25 µL Buffer FTB, and 20 µL proteinase K. In contrast to Group A, the tissues were then heat-treated at 75° C. for 1 hour to de-crosslink. After the heat treatment, the tissues were centrifuged and transferred to new microcentrifuge tubes. Then, 115 µL RNase-free water and 35 µL of the enzyme uracil-N-glycosylase (UNG) were added to the samples to remove artifacts of deaminated cytosine residues of the FFPE DNA. In contrast to Group A, here the sampled were incubated with UNG at 50° C. for 30 minutes. After incubation, the samples were cooled down to room temperature, 2 µL Mung Bean Nuclease (10 units/µL, New England BioLabs) was added to each sample, and the samples were incubated for 30 minutes at 30° C. to cleave single-stranded DNA regions and basepair mismatches. The samples were then treated with 2 µL RNase A at room temperature for 2 minutes. To harvest the DNA, the QIAamp MinElute columns were used to bind the DNA while contaminants were removed by buffer-wash and centrifugal steps as specified in the DNA purification protocol. Finally, DNA was eluted in 20 µL Buffer ATE. The amount of extracted DNA was quantified by the Qubit fluorometer.

The extracted genomic DNA was diluted in 10 mM Tris-HCl (pH 8.0-8.5) to 35 µL. To fragment the genomic DNA, 10 µL KAPA Frag Enzyme and 5 µL 10× KAPA Frag Buffer were added, and the enzymatic reaction was incubated for 30 minutes at 37° C., then held at 4° C. Subsequent to the DNA fragmentation, end repair and A-tailing of the fragments were performed by adding 7 µL End Repair & A-Tailing Buffer and 3 µL End Repair & A-Tailing Enzyme Mix, and rapidly heating up to 65° C. and incubating at 65° C. for 30 minutes. Then, adapter ligation was performed by adding 5 µL Adapter stock, 5 µL PCR-grade water, 30 µL Ligation Buffer, and 10 µL DNA Ligase, and incubating at 20° C. for 15 minutes.

To clean up the reaction, 88 µL KAPA Pure Beads was added. The sample was mixed thoroughly and incubated at room temperature for 10 minutes to bind DNA to the beads. The DNA and beads were captured by a magnet during several ethanol washes according to the library construction protocol, and then resuspended in 25 µL elution buffer (10 mM Tris-HCl, pH 8.0-8.5). To elute DNA off the beads, the sample was incubated at room temperature for 2 minutes. The beads were captured by the magnet while 20 µL of the supernatant containing the DNA was transferred to a new microcentrifuge tube. After cleaning up the reaction, the DNA library fragments carrying appropriate adapter sequences were amplified by PCR. 5 µL Library Amplification Primer Mix and 25 µL KAPA HiFi HotStart ReadyMix, containing the low-bias, high-fidelity KAPA HiFi HotStart DNA Polymerase, were added. A PCR cycle specified in the library construction protocol and a post-amplification cleanup, again using magnetic KAPA Pure Beads, were performed.

Example 5

DNA Extraction and Library Preparation—Group F

Three FFPE slides of low quality, moderate quality, and high quality, respectively, were processed according to the DNA purification protocol of Qiagen GeneRead DNA FFPE Kit, followed by the library construction protocol of KAPA HyperPlus Kit, but with some modifications.

Briefly, the slides were dewaxed by warming at 56° C. in 160 µL Deparaffinization Solution for 3 minutes. The tissues were lysed at 56° C. for 1 hour in 55 µL RNase-free water, 25 µL Buffer FTB, and 20 µL proteinase K. In contrast to Group A, the tissues were then heat-treated at 75° C. for 1 hour to de-crosslink. After the heat treatment, the tissues were centrifuged and transferred to new microcentrifuge tubes. Then, 115 µL RNase-free water and 35 µL of the enzyme uracil-N-glycosylase (UNG) were added to the samples, and the samples were incubated at 50° C. for 1 hour to remove artifacts of deaminated cytosine residues of the FFPE DNA. The samples were then treated with 2 µL RNase A at room temperature for 2 minutes. To harvest the DNA, the QIAamp MinElute columns were used to bind the DNA while contaminants were removed by buffer-wash and centrifugal steps as specified in the DNA purification protocol. Finally, DNA was eluted in 20 µL Buffer ATE. The amount of extracted DNA was quantified by the Qubit fluorometer.

The extracted genomic DNA was diluted in 10 mM Tris-HCl (pH 8.0-8.5) to 35 µL. To fragment the genomic DNA, in contrast to Group A, 0.1 µL Mung Bean Nuclease (10 units/µL, New England BioLabs), 10 µL KAPA Frag Enzyme and 5 µL 10× KAPA Frag Buffer were added, and the enzymatic reaction was incubated for 30 minutes at 30° C., then held at 4° C. Subsequent to the DNA fragmentation, end repair and A-tailing of the fragments were performed by adding 7 µL End Repair & A-Tailing Buffer and 3 µL End Repair & A-Tailing Enzyme Mix, and rapidly heating up to 65° C. and incubating at 65° C. for 30 minutes. Then, adapter ligation was performed by adding 5 µL Adapter stock, 5 µL PCR-grade water, 30 µL Ligation Buffer, and 10 µL DNA Ligase, and incubating at 20° C. for 15 minutes.

To clean up the reaction, 88 µL KAPA Pure Beads was added. The sample was mixed thoroughly and incubated at room temperature for 10 minutes to bind DNA to the beads. The DNA and beads were captured by a magnet during several ethanol washes according to the library construction protocol, and then resuspended in 25 µL elution buffer (10 mM Tris-HCl, pH 8.0-8.5). To elute DNA off the beads, the sample was incubated at room temperature for 2 minutes. The beads were captured by the magnet while 20 µL of the supernatant containing the DNA was transferred to a new microcentrifuge tube. After cleaning up the reaction, the DNA library fragments carrying appropriate adapter sequences were amplified by PCR. 5 µL Library Amplification Primer Mix and 25 µL KAPA HiFi HotStart ReadyMix, containing the low-bias, high-fidelity KAPA HiFi HotStart DNA Polymerase, were added. A PCR cycle specified in the library construction protocol and a post-amplification cleanup, again using magnetic KAPA Pure Beads, were performed.

Example 6

DNA Extraction and Library Preparation—Group G

Three FFPE slides of low quality, moderate quality, and high quality, respectively, were processed according to the DNA purification protocol of Qiagen GeneRead DNA FFPE Kit, followed by the library construction protocol of KAPA HyperPlus Kit, but with some modifications.

Briefly, the slides were dewaxed by warming at 56° C. in 160 µL Deparaffinization Solution for 3 minutes. The tissues were lysed at 56° C. for 1 hour in 55 µL RNase-free water, 25 µL Buffer FTB, and 20 µL proteinase K. In contrast to Group A, the tissues were then heat-treated at 75° C. for 1 hour to de-crosslink. After the heat treatment, the tissues were centrifuged and transferred to new microcentrifuge tubes. Then, 115 µL RNase-free water and 35 µL of the enzyme uracil-N-glycosylase (UNG) were added to the samples, and the samples were incubated at 50° C. for 1 hour to remove artifacts of deaminated cytosine residues of the FFPE DNA. The samples were then treated with 2 µL RNase A at room temperature for 2 minutes. To harvest the DNA, the QIAamp MinElute columns were used to bind the DNA while contaminants were removed by buffer-wash and centrifugal steps as specified in the DNA purification protocol. Finally, DNA was eluted in 20 µL Buffer ATE. The amount of extracted DNA was quantified by the Qubit fluorometer.

The extracted genomic DNA was diluted in 10 mM Tris-HCl (pH 8.0-8.5) to 35 µL. To fragment the genomic DNA, in contrast to Group A, 0.1 µL RecJ$_f$ (30 units/µL, New England BioLabs), 10 µL KAPA Frag Enzyme and 5 µL 10× KAPA Frag Buffer were added, and the enzymatic reaction was incubated for 30 minutes at 37° C., then held at 4° C. Subsequent to the DNA fragmentation, end repair and A-tailing of the fragments were performed by adding 7 µL End Repair & A-Tailing Buffer and 3 µL End Repair & A-Tailing Enzyme Mix, and rapidly heating up to 65° C. and incubating at 65° C. for 30 minutes. Then, adapter ligation was performed by adding 5 µL Adapter stock, 5 µL PCR-grade water, 30 µL Ligation Buffer, and 10 µL DNA Ligase, and incubating at 20° C. for 15 minutes.

To clean up the reaction, 88 µL KAPA Pure Beads was added. The sample was mixed thoroughly and incubated at room temperature for 10 minutes to bind DNA to the beads. The DNA and beads were captured by a magnet during several ethanol washes according to the library construction protocol, and then resuspended in 25 µL elution buffer (10 mM Tris-HCl, pH 8.0-8.5). To elute DNA off the beads, the sample was incubated at room temperature for 2 minutes. The beads were captured by the magnet while 20 µL of the supernatant containing the DNA was transferred to a new microcentrifuge tube. After cleaning up the reaction, the DNA library fragments carrying appropriate adapter sequences were amplified by PCR. 5 µL Library Amplification Primer Mix and 25 µL KAPA HiFi HotStart ReadyMix, containing the low-bias, high-fidelity KAPA HiFi HotStart DNA Polymerase, were added. A PCR cycle specified in the library construction protocol and a post-amplification cleanup, again using magnetic KAPA Pure Beads, were performed. Table 1 below shows a summary of the preparations from each of Groups A, B, E, F and G.

TABLE 1

Protocol modifications for the five experimental groups.

| Group | Decrosslinking | UNG treatment | Fragmentation |
|---|---|---|---|
| A | None | None | None |
| B | None | Reduce incubation time at 50° C. to 30 min. After incubation, cool to room temp and add 2 uL MBN. Incubate for 30 min at 30° C. | None |

TABLE 1-continued

Protocol modifications for the five experimental groups.

| Group | Decrosslinking | UNG treatment | Fragmentation |
|---|---|---|---|
| E | Incubate 75° C. | Reduce incubation time at 50° C. to 30 min. After incubation, cool to room temp and add 2 uL MBN. Incubate for 30 min at 30° C. | None |
| F | Incubate 75° C. | None | Add 0.1 µL MBN and reduce incubation to 30° C. Make sure subsequent heating from 4° C. to 65° C. is rapid. |
| G | Incubate 75° C. | None | Add 0.1 µL RecJf. Make sure subsequent heating from 4° C. to 65° C. is rapid. |

*MBN = mung bean nuclease

Example 7

DNA Sequencing Analysis

The libraries prepared as discussed above for Groups A, B, E, F, and G conditions for the FFPE slides of low quality, moderate quality, and high quality, were sequenced on the Illumina NextSeq using 2×150 chemistry. Standard library metrics were determined.

Figure 2:
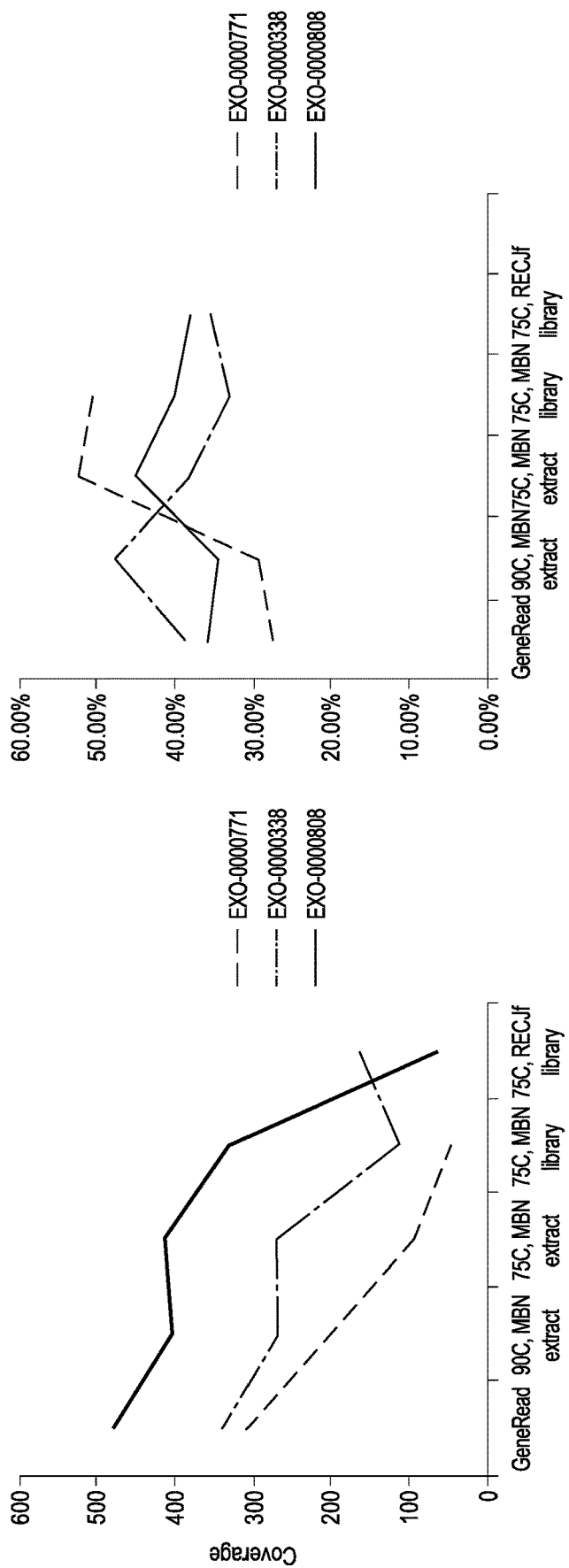
FIG. 2 shows the relationship between sequencing coverage (left panel) or variance (right panel) of the sequencing libraries and preparation conditions (x-axis) for FFPE samples of low quality (EXO-0000771), moderate quality (EXO-0000338), and high quality (EXO-0000808).

The sequencing coverage results are shown in FIG. 2. It was discovered that preparation conditions Group B and Group E, in which the samples were treated with Mung Bean Nuclease during UNG incubation, had similar amounts of coverage despite substantially different Qubit quantifications. It was likely that there were similar amounts of high quality DNA in each, but the 90° C. de-crosslinking treatment of Group B additionally resulted in large amounts of low quantity DNA. To maximize coverage but not Qubit quantifications, the 75° C. de-crosslinking treatment of Group E showed satisfactory results. There did not seem to be much effect of preparation conditions on variance.

Figure 3:
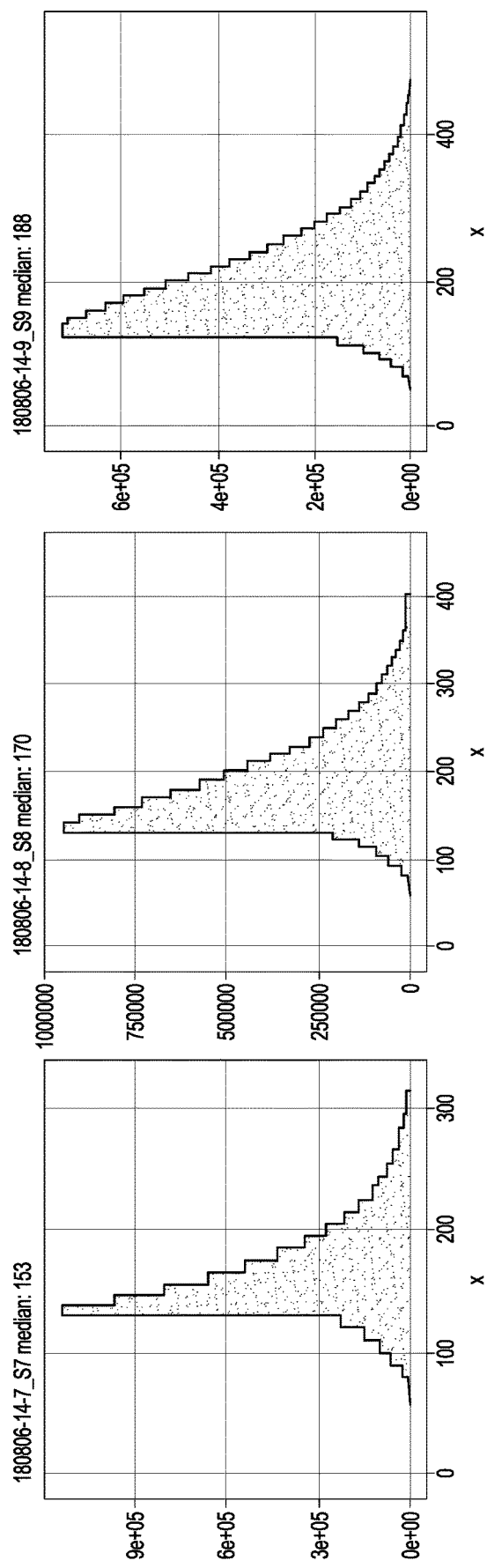
FIG. 3 shows the fragment size distribution of the sequencing libraries of preparation condition Group E for FFPE samples of low quality (EXO-0000771, left panel), moderate quality (EXO-0000338, center panel), and high quality (EXO-0000808, right panel).

The fragment size distribution results of the sequencing libraries of preparation condition Group E are shown in FIG. 3. Higher quality samples tended to have higher fragment size, as expected. The non-symmetry was caused by the BAM filter, which removed reads without enough matching bases or those with low mapq, which could be caused by short insert length.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products. For example, any of the components for an energy storage system described herein can be provided separately, or integrated together (e.g., packaged together, or attached together) to form an energy storage system.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" represent a value, amount, or characteristic close to the stated value, amount, or characteristic that still performs a desired function or achieves a desired result.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of analyzing a tissue sample, comprising:
   i) obtaining a tissue sample comprising tissue DNA that comprises double-stranded DNA (dsDNA) suspected of having one or more thymine lesions formed by deamination of 5-methylcytosines, wherein the thymine lesions form base pair mismatches in the dsDNA;
   ii) lysing the tissue sample to form lysed tissue;
   iii) contacting the lysed tissue with a nuclease that digests dsDNA at base pair mismatches;
   iv) after step iii), harvesting DNA from the lysed tissue; and
   v) performing an analysis on undigested DNA harvested in step iv).

2. The method of claim 1, wherein the nuclease comprises Mung Bean Nuclease, CEL I, Surveyor nuclease, *aspergillus* nuclease S1, P1 nuclease, BAL 31, T4 endonuclease VII, T7 endonuclease I, endonuclease V, EndoMS, RecJ$_f$, or any combination thereof.

3. The method of claim 2, wherein the lysed tissue is further contacted with uracil-N-glycosylase, uracil-DNA glycosylase, thymine DNA glycosylase, methyl-CpG-binding protein 4, or any combination thereof, to remove mismatched DNA bases.

4. The method of claim 1, wherein the tissue sample is a formalin-fixed paraffin-embedded (FFPE) tissue sample, fresh-frozen sample, freshly cut curls, or freshly cut slides.

5. The method of claim 1, wherein the tissue sample is obtained from the bone, bone marrow, breast, mouth, nasopharynx, esophagus, stomach, duodenum, rectum, colon, intestine, appendix, pancreas, lung, liver, prostate, nervous system, heart, bladder, kidney, cervix, uterus, ovary, lymph node, thyroid, muscle, or skin of a subject, the subject being a mammal.

6. The method of claim 5, wherein the subject is a patient having a refractory disease or a cancer.

7. The method of claim 1, wherein obtaining a tissue sample comprises a stereotactic biopsy, open biopsy, or surgical resection.

8. The method of claim 1, wherein performing the analysis comprises performing a next-generation DNA sequencing analysis on:
   single nucleotide variants and insertions/deletions up to 40 basepairs in coding regions of a plurality of target genes;
   gene copy number variations;
   untranslated regions and splice junctions of the DNA;
   gene fusions;
   microsatellite instability; and/or
   tumor mutation burden.

9. The method of claim 8, wherein performing a next-generation DNA sequencing analysis comprises tagging each strand of DNA with duplex unique molecular identifier (UMI).

10. The method of claim 8, wherein performing a next-generation DNA sequencing analysis comprises amplifying DNA with a low bypass efficiency DNA polymerase.

11. The method of claim 10, wherein the DNA polymerase comprises Pfu or KAPA.

12. The method of claim 8, wherein the plurality of target genes comprise:
   ABCB1, ABCC1, ABCC2, ABL1, ADAMTS1, ADAMTS16, ADAMTS18, ADAMTS6, ADAMTS9, ADAMTSL1, AKT1, AKT2, AKT3, ALK, AMER1, APC, APLNR, AR, ARAF, AREG, ARID1A, ARID1B, ARID2, ATM, ATR, ATRX, AURKA, AURKB, AXIN1, AXL, B2M, BAP1, BARD1, BCOR, BNIP3, BRAF, BRCA1, BRCA2, BRIP1, BTK, BUB1B, CBL, CCND1, CCND2, CCND3, CCNE1, CD274, CDA, CDC73, CDH1, CDK12, CDK4, CDK6, CDKN2A, CHEK1, CHEK2, CHFR, CHKA, CIC, CREBBP, CSF1R, CTLA4, CTNNB1, CYP19A1, CYP1A1, CYP2D6, CYP3A4, CYSLTR2,DCK, DDR2, DICER1, DNMT3A, EGFR, EMSY, EP300, EPCAM, EPHA5, EPHA7, ERBB2, ERBB3, ERBB4, ERCC1, ERCC2, ERCC3, ERRFI1, ESR1, ESR2, EWSR1, EZH2, FAM175A, FANCA, FANCC, FANCD2, FANCE, FANCF, FANCG, FANCM, FAT1, FBXW7, FCGR2A, FGD4, FGF3, FGF4, FGFR1, FGFR2, FGFR3, FGFR4, FLT3, FLT4, FOXL2, FUBP1, GATA3, GLI1, GNA11, GNAQ, GNAS, GSTP1, GSTT1, HDAC2, HGF, HNF1A, HRAS, HSD3B1, IDH1, IDH2, IGF1R, IKZF1, JAK1, JAK2, JAK3, KDM5C, KDM6A, KDR, KEAP1, KIT, KRAS, MAF, MAP2K1, MAP2K2, MAP3K1, MAPK1, MAPK3, MAPKAPK5, MDM2, MDM4, MED12, MEN1, MET, MGMT, MLH1, MRE11A, MSH2, MSH6, MTHFR, MTOR, MUTYH, MYC, MYCN, MYOD1, NBN, NF1, NF2, NFE2L2, NOTCH1, NOTCH2, NOTCH3, NPM1, NRAS, NTRK1, NTRK2, NTRK3, PALB2, PBRM1, PDCD1LG2, PDGFRA, PDGFRB, PIK3CA, PIK3CB, PIK3CD, PIK3CG, PIK3R1, PLCB4, PLCG1, PMS2, POLD1, POLE, PPP2R1A, PTCH1, PTEN, PTPN11, RAD50, RAD51C, RAD51D, RAF1, RB1, RBM10, RECQL, RET, RHEB, RICTOR, RIT1, RNF43, ROS1, RPTOR, RRM1, SDHB, SDHC, SETD2, SF3B1, SMAD2, SMAD4, SMARCA4, SMARCB1, SMO, SOCS1, SPOP, STAG2, STAT5, STK11, SUFU, TERT-p, TGFBR2, TNFAIP3, TOP2A, TP53, TSC1, TSC2, TSHR, TYMS, VEGFA, VHL, WT1, XRCC1, and YES1.

13. The method of claim 1, further comprising performing an analysis on mRNA expression and/or gene isoforms of a plurality of target genes, the analysis comprising in situ hybridization, reverse transcription-polymerase chain reaction, microarray, nuclease protection assays, or RNA sequencing.

14. The method of claim 13, wherein the plurality of target genes comprise:
AR, AREG, ARID1A, BAD, BAX, BCL2, BIRC5, BRCA1, CA9, CDA, CDH1, CES2, CHUK, DCK, DHFR, DPYD, EPHA2, ERBB2, ERBB3, ERCC1, EREG, ESR1, EZH2, FGFR1, IGF1R, KDR, KIT, LRP6, MET, MGMT, MITF, MTOR, NFKB1, PARP1, PDGFRB, PGR, PTEN, PTGS2, PTPN6, RELA, RPS6KB1, RRM1, SLC29A1, SSTR2, TNFSF13, TOP2A, TUBB3, TYMP, TYMS, VEGFA, EGFR VIII, and MET EXON 14 SKIPPING.

15. The method of claim 1, further comprising performing an immunohistochemistry analysis on a plurality of target proteins.

16. The method of claim 15, wherein the plurality of target proteins comprise: ALK, AR, CAIX, ER, hENT1, HER2/neu, PD1, PD-L1, PMS2, PR, PTEN, RET, IDO, MET, MGMT, MLH1, MSH2, MSH6, ROS1, TOPO1, TP, TRKpan, TS, and TUBB3.

17. The method of claim 1, wherein performing the analysis comprises performing a cancer diagnosis and, optionally, detecting DNA mismatch repair deficiency.

18. The method of claim 17, wherein the cancer comprises breast cancer, colorectal cancer, lynch syndrome, non-small-cell lung carcinoma, acute lymphoblastic leukemia, acute myeloid leukemia, adrenocortical carcinoma, aids-related cancers, Kaposi sarcoma, aids-related lymphoma, primary CNS lymphoma, anal cancer, appendix cancer, astrocytomas, atypical teratoid/rhabdoid tumor, basal cell carcinoma of the skin, bile duct cancer, bladder cancer, bone cancer, brain tumors, bronchial tumors, Burkitt lymphoma, carcinoid tumor, carcinoma of unknown primary, cardiac tumors, cervical cancer, cholangiocarcinoma, chronic lymphocytic leukemia, chronic myelogenous leukemia, chronic myeloproliferative neoplasms, craniopharyngioma, cutaneous T-cell lymphoma, ductal carcinoma in situ, embryonal tumors, endometrial cancer, esophageal cancer, esthesioneuroblastoma, Ewing sarcoma, extragonadal germ cell tumor, eye cancer, intraocular melanoma, retinoblastoma, fallopian tube cancer, fibrous histiocytoma of bone, gallbladder cancer, gastric cancer, gastrointestinal carcinoid tumor, gastrointestinal stromal tumors, germ cell tumors, extragonadal germ cell tumors, ovarian germ cell tumors, testicular cancer, gestational trophoblastic disease, hairy cell leukemia, head and neck cancer, hepatocellular cancer, histiocytosis, Hodgkin lymphoma, hypopharyngeal cancer, intraocular melanoma, islet cell tumors, pancreatic neuroendocrine tumors, kidney cancer, Langerhans cell histiocytosis, laryngeal cancer, leukemia, lip and oral cavity cancer, liver cancer, non-small cell lung cancer, lymphoma, male breast cancer, malignant fibrous histiocytoma of bone and osteosarcoma, melanoma, intraocular melanoma, Merkel cell carcinoma, mesothelioma, metastatic cancer, metastatic squamous neck cancer with occult primary, midline tract carcinoma with nut gene changes, mouth cancer, multiple endocrine neoplasia syndromes, multiple myeloma/plasma cell neoplasms, mycosis fungoides, myelodysplastic syndromes, myelodysplastic/myeloproliferative neoplasms, myelogenous leukemia, myeloid leukemia, nasal cavity and paranasal sinus cancer, nasopharyngeal cancer, neuroblastoma, non-Hodgkin lymphoma, oral cancer, osteosarcoma and malignant fibrous histiocytoma of bone, ovarian cancer, pancreatic cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, plasma cell neoplasm/multiple myeloma, pleuropulmonary blastoma, primary central nervous system lymphoma, primary peritoneal cancer, prostate cancer, rectal cancer, recurrent cancer, renal cell cancer, retinoblastoma, rhabdomyosarcoma, salivary gland cancer, sarcoma, osteosarcoma, soft tissue sarcoma, uterine sarcoma, Sézary syndrome, skin cancer, small cell lung cancer, small intestine cancer, squamous cell carcinoma of the skin, stomach cancer, testicular cancer, throat cancer, nasopharyngeal cancer, oropharyngeal cancer, hypopharyngeal cancer, thymoma and thymic carcinoma, thyroid cancer, transitional cell cancer of the renal pelvis and ureter, urethral cancer, endometrial uterine cancer, uterine sarcoma, vaginal cancer, vascular tumors, vulvar cancer, and/or Wilms tumor.

19. The method of claim 17, further comprising:
screening for one or more therapies according to the cancer diagnosis; and
producing a computer-generated report of therapies with potential increased benefit and therapies with potential reduced benefit.

20. The method of claim 19, wherein the one or more therapies comprise:
Abemaciclib, Abiraterone, Ado-trastuzumab emtansine, Afatinib, Alectinib, Anastrozole, Atezolizumab, Avelumab, Bevacizumab, Bicalutamide, Binimetinib, Brigatinib, Cabozantinib, Capecitabine, Carboplatin, Carmustine, Ceritinib, Cetuximab, Cisplatin, Crizotinib, Dabrafenib, Dacarbazine, Dacomitinib, Dasatinib, Diethylstilbestrol, Dinutuximab, Docetaxel, Doxorubicin, Durvalumab, Encorafenib, Enzalutamide, Epirubicin, Eribulin, Erlotinib, Everolimus, Exemestane, Fluorouracil, Flutamide, Fulvestrant, Gefitinib, Gemcitabine, Idelalisib, Imatinib, Interleukin-2, Ipilimumab, Irinotecan, Ketoconazole, Lapatinib, Lenvatinib, Letrozole, Liposomal Doxorubicin, Lorlatinib, Medroxy-progesterone, Megestrol, Mitomycin, Neratinib, Nilotinib, Nintedanib, Niraparib, Nivolumab, Olaparib, Olaratumab, Osimertinib, Oxaliplatin, Paclitaxel, Palbociclib, Panitumumab, Pazopanib, Pembrolizumab, Pemetrexed, Pertuzumab, Procarbazine, Regorafenib, Ribociclib, Rucaparib, Sonidegib, Sorafenib, Streptozocin, Sunitinib, Talazoparib, Tamoxifen, Temozolomide, Temsirolimus, Topotecan, Toremifene, Trametinib, Trastuzumab, Vandetanib, Vemurafenib, Vincristine, Vismodegib, Zoledronic acid, or any combination thereof.

* * * * *